United States Patent [19]
Schmidt

[11] Patent Number: 5,972,013
[45] Date of Patent: Oct. 26, 1999

[54] DIRECT PERICARDIAL ACCESS DEVICE WITH DEFLECTING MECHANISM AND METHOD

[75] Inventor: Cecil C. Schmidt, Edina, Minn.

[73] Assignee: Comedicus Incorporated, Columbia Heights, Minn.

[21] Appl. No.: 08/934,045

[22] Filed: Sep. 19, 1997

[51] Int. Cl.$^6$ ................................................ A61M 29/00
[52] U.S. Cl. .......................................... 606/185; 604/164
[58] Field of Search ................................ 606/184, 185; 604/115, 264, 164, 272

[56] References Cited

U.S. PATENT DOCUMENTS

| | | |
|---|---|---|
| 3,923,060 | 12/1975 | Ellinwood, Jr. . |
| 4,003,379 | 1/1977 | Ellinwood, Jr. . |
| 4,808,157 | 2/1989 | Coombs ................................ 604/272 |
| 4,958,901 | 9/1990 | Coombs ................................ 604/272 |
| 4,991,578 | 2/1991 | Cohen . |
| 5,071,412 | 12/1991 | Noda . |
| 5,087,243 | 2/1992 | Avitall . |
| 5,213,570 | 5/1993 | VanDeripe . |
| 5,220,917 | 6/1993 | Cammilli et al. . |
| 5,269,326 | 12/1993 | Verrier . |
| 5,336,252 | 8/1994 | Cohen . |
| 5,387,419 | 2/1995 | Levy et al. . |
| 5,681,278 | 10/1997 | Igo et al. . |

FOREIGN PATENT DOCUMENTS

WO 98/05289  2/1998  WIPO .

OTHER PUBLICATIONS

Product Description Sheet by Comedicus Incorporated for A New Approach: Access The Pericardial Space With The PerDucer™ Pericardial Access Device.

Medical Device & Diagnostic Industry, Advertisement, "Spectrum . . . precision from start to finish".

Advertisement "Corrosion–Resistant Alloys", Ulbrich Stainless Steels & Special Metals Inc.

Surgical Instruments, Advertisement for T.A.G. Medical Products Ltd.

*Primary Examiner*—Michael Buiz
*Assistant Examiner*—William Lewis
*Attorney, Agent, or Firm*—Merchant & Gould P.C.

[57] ABSTRACT

The invention is directed to a device and method for minimally invasive access to the pericardial space of a human or animal patient. The disclosed pericardial access device includes a penetrating body axially mobile within the lumen of a guide tube. The guide tube includes a deflecting mechanism for deflecting the distal end of the penetrating body. In use, a patient's pericardium is contacted with the distal end of the guide tube and suction is applied to form a pericardial bleb. The penetrating body is axially mobilized distally within the lumen of the guide tube until the deflecting mechanism deflects the penetrating body to cause the penetrating end of the penetrating body to enter the bleb of pericardial tissue at an angle oblique to the longitudinal axis of the guide tube.

18 Claims, 6 Drawing Sheets

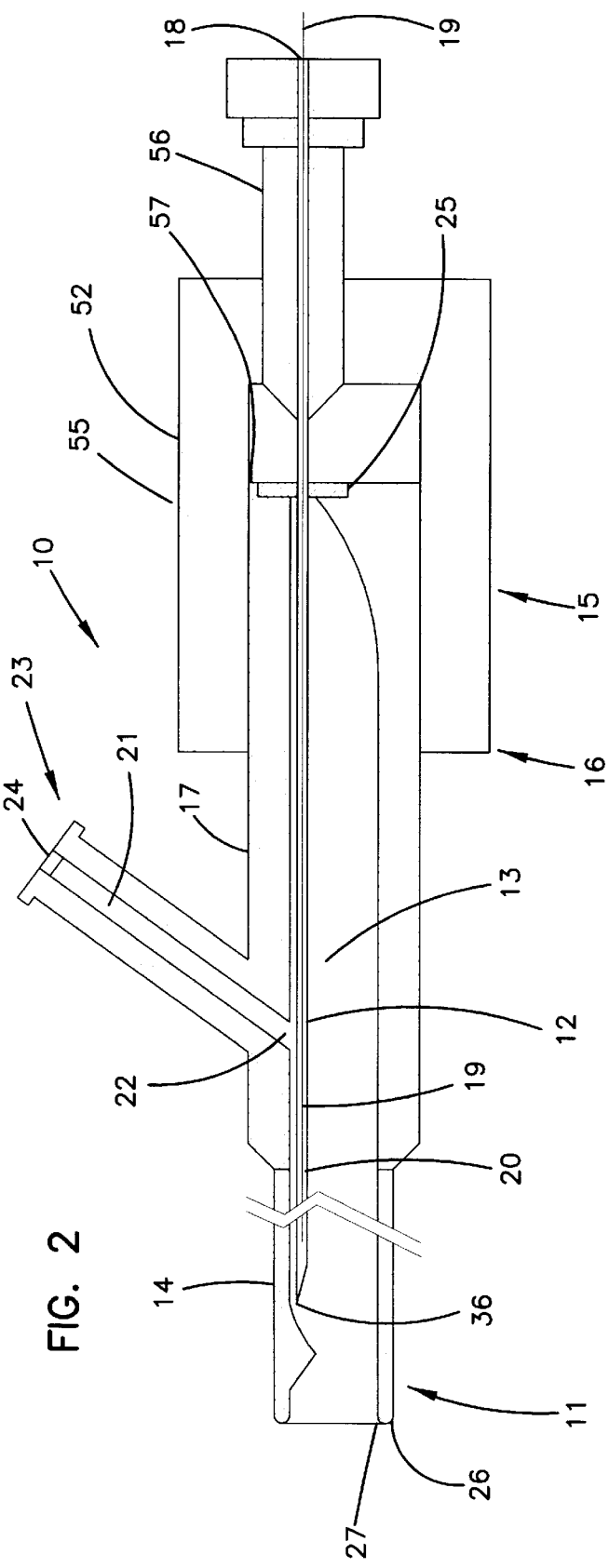
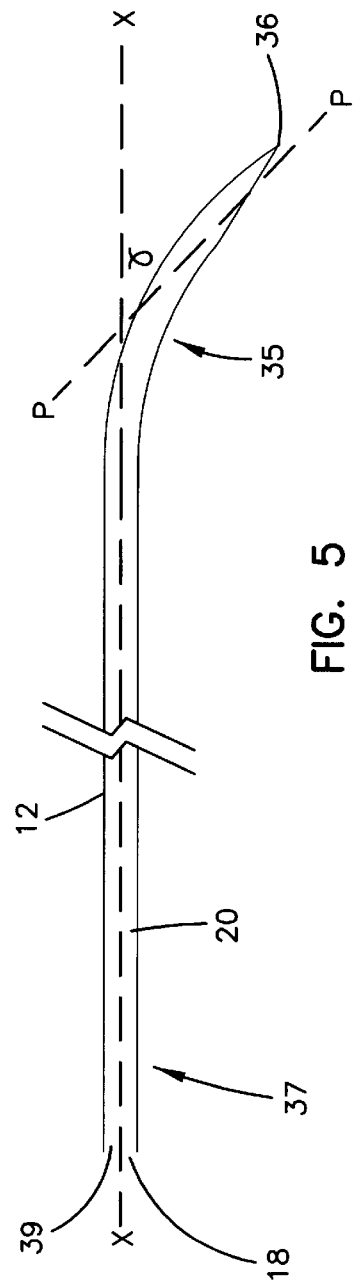
FIG. 2
FIG. 5

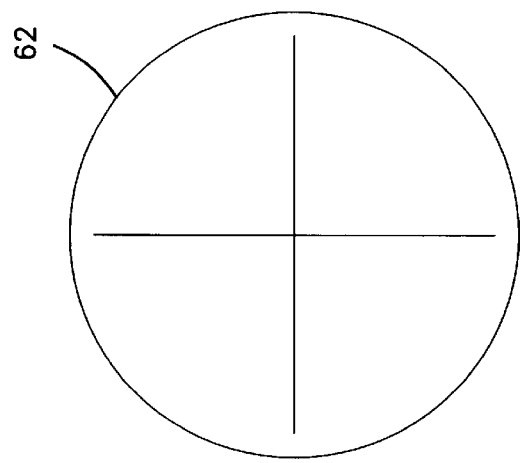
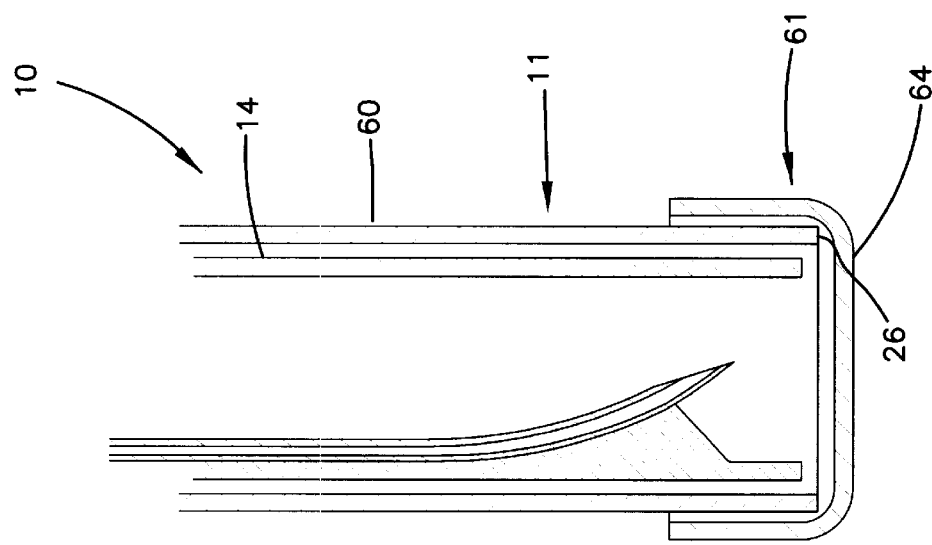
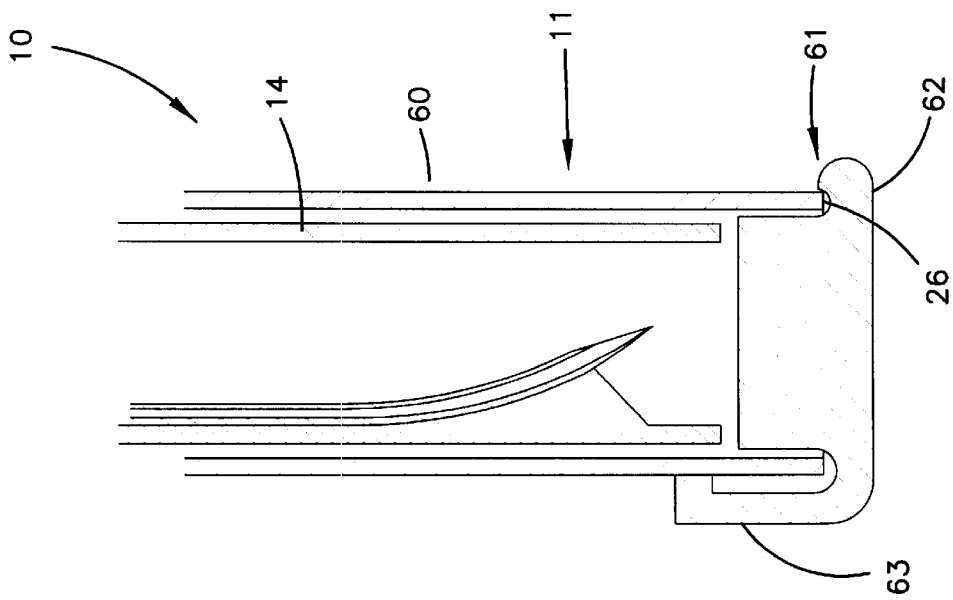
FIG. 7
FIG. 8
FIG. 9

DIRECT PERICARDIAL ACCESS DEVICE WITH DEFLECTING MECHANISM AND METHOD

FIELD OF THE INVENTION

The present disclosure is directed to minimally invasive cardiac procedures. More specifically, the disclosure provides a device and method for accurate local access to the pericardial space with reduced risk of injury to the myocardium and associated coronary vessels.

BACKGROUND OF THE INVENTION

Knowledge of the pericardium (pericardial sac) dates back to the time of Galen (129–200 A.D.) the Greek physician and anatomist who created the term "pericardium." The pericardium (pericardial sac) is a conical membranous sac in which the heart and the commencement of the great vessels are contained. Gray's Anatomy (1977 ed.) pp. 457–460. The pericardium is fluid-filled and functions to prevent dilation of the chambers of the heart, lubricates the surfaces of the heart, and maintains the heart in a fixed geometric position. It also provides a barrier to the spread of infection from adjacent structures in the chest cavity and prevents surrounding tissue(s) from adhering to the heart. The space between the pericardium and the heart, known as the pericardial space, is normally small in volume and includes the fluid therein. It has been reported by others that when fluid is injected into the pericardial space it accumulates in the atrioventricular and interventricular grooves, but not over the ventricular surfaces. See, Shabetai R, "Pericardial and Cardiac Pressure," in *Circulation*, 77:1 (1988).

Pericardiocentesis, or puncture of the pericardium, heretofore has been performed for: 1) diagnosis of pericardial disease(s) by study of the pericardial fluid; 2) withdrawal of pericardial fluid for the treatment of acute cardiac tamponade; and 3) infusion of therapeutic agents for the treatment of malignant effusion or tumors. Thus, at present, intrapericardial injection of drugs is clinically limited to the treatment of abnormal pericardial conditions and diseases, such as malignant or loculated pericardial effusions and tumors. Drugs that have been injected into the pericardial space include antibiotic (sclerosing) agents, such as tetracycline and bleomycin or fibrinolytic agents such as streptokinase.

Intrapericardial drug delivery has not been clinically utilized for heart-specific treatments where pericardial pathology is normal, because the pericardial space is normally small and very difficult to access without invasive surgery or risk of cardiac injury by standard needle pericardiocentesis techniques. Normally, pericardiocentesis procedures are carried out by highly specialized, personnel in the cardiac catheterization laboratory of medical facilities, assisted by fluoroscopy and electrocardiogram monitoring equipment. Electrocardiographic monitoring of pericardiocentesis, using the pericardial needle as an electrode is commonly employed, as disclosed in Bishop L. H., et al., "The Electrocardiogram as a Safeguard in Pericardiocentesis," in *JMA*, 162:264 (1956), and Neill J. R., et al., "A Pericardiocentesis Electrode," in *The New England Journal of Medicine*, 264:711 (1961); Gotsman M. S., et al. "A Pericardiocentesis Electrode Needle," in *Br. Heart J.*, 28:566 (1966); and Kerber R. E., et al., "Electrocardiographic Indications of Atrial Puncture During Pericardiocentesis," in *The New England Journal of Medicine*, 282:1142 (1970). An echocardiographic transducer with a central lumen has also been used to guide the pericardiocentesis needle as reported in Goldberg B. B., et al., "Ultrasonically Guided Pericardiocentesis," in *Amer. J. Cardiol.*, 31:490 (1973).

However, there are complications associated with needle pericardiocentesis. These complications include laceration of a coronary artery or the right ventricle, perforation of the right atrium or ventricle, puncture of the stomach or colon, pneumothorax, arrhythmia, tamponade, hypertension, ventricular fibrillation, and death. Complication rates for needle pericardiocentesis are increased in situations where the pericardial space and fluid effusion volume is small (i.e., the pericardial size is more like normal and not abnormally distended by the accumulation of fluid, e.g., blood).

U.S. Pat. No. 5,071,428 (Chin et al.) discloses a method and apparatus for accessing the pericardial space for the insertion of implantable defibrillation leads. This method requires gripping the pericardium with a forceps device and cutting the pericardium with a scalpel (pericardiotomy) under direct vision through a subxiphoid surgical incision.

Uchida Y., et al., "Angiogenic Therapy of acute Myocardial Infarction by Intrapericardial Injection of Basic Fibroblast Growth Factor and Heparin Sulfate," in *Circulation AHA Abstracts* (1994), reported a method for the intrapericardial injection of angiogenic agents. While not described in detail, this method generally involved the percutaneous transcatheter bolus injection of drugs into the pericardial cavity via the right atrium. A major drawback of this method is that the right atrial wall is crossed, that could lead to bleeding into the pericardial space. In addition, the method involved the bolus injection of drugs rather than long-term delivery via a catheter of controlled release material.

U.S. Pat. No. 4,991,578 (Cohen) discloses an apparatus for accessing the pericardial space for placement of defibrillation electrodes. The apparatus disclosed uses suction to "pull" the pericardium against a perforating needle housed in an outer catheter, thus impaling the pericardium on the needle (col. 15, lines 54–57). One of the stated problems with the apparatus is loss of suction. Col. 15, lines 4–5. A solution to the loss of suction proposed in the patent is to apply suction to pull the pericardium into the lumen of the catheter, apply a wire suture to stabilize the catheter tip and subsequently advance a piercing needle into the pericardium sutured to the catheter. In addition to other disadvantages, the added step of suturing in this method is undesirable.

Another method for intrapericardial injection of agents is performed by a device, available under the name PerDUCER™ pericardial access device, available from Comedicus Incorporated, 3839 Central Avenue, NE, Columbia Heights, Minn. 55431. This device uses suction to create a lifted section of the pericardium, known as a "bleb." Specifically, the bleb is secured to an elongate access device by a vacuum force exerted through a side wall port that is in a plane substantially parallel to the longitudinal access of the device. Once formed, the bleb is punctured by a needle of limited travel that penetrates the bleb in a direction tangential to the epicardial surface of the heart. While creating a bleb by suction through a side wall port combined with a tangential needle approach to the bleb can reduce the chance of puncturing or lacerating the myocardium, accurately penetrating the pericardium at a desired location may be difficult due to the motion of the heart during normal cardiac contraction relative to the orientation of the axial dimension of the device.

Accordingly, there is a need for a system for accurate localized penetration of the pericardium which has low risk of causing penetration or laceration of the myocardium. Moreover, there is a need to effectively penetrate the pericardium without the chance of loss of vacuum and repeated attempts to effect penetration.

SUMMARY OF THE INVENTION

The present invention provides a device and method for access to the pericardial space without injury to the heart, in order to aspirate fluids directly from or to directly deliver fluids, i.e., therapeutic drugs, to the heart muscle or associated vasculature. With such safe access to the heart, complications from contacting the heart muscle are greatly reduced and nearly eliminated. Additionally, by directly delivering drugs to the heart muscle via the pericardium (pericardial sac), side affects associated with drug delivery by conventional administration methods, i.e., oral or injection, can be reduced, such that lesser dosages are needed to achieve the desired effect of a specific drug. Moreover, the present method for direct delivery of a drug provides for a wider range of drugs to be used.

A pericardial access device according to the invention includes a penetrating body having a piercing distal tip. The penetrating body is axially mobile within the lumen of a guide tube. The guide tube has a proximal end for handling and operating the pericardial access device. The distal end of the guide tube has a distal port opening into the lumen of the guide tube. Within the distal end of the guide tube there is also a deflecting mechanism for deflecting the penetrating end of the penetrating body as it is advanced towards the distal port of the device. In one embodiment, the deflecting mechanism is a deflecting wedge. In an alternative embodiment, the deflecting mechanism is a deflecting tube.

According to the invention, a suction or aspiration force is applied to the lumen of the guide tube to form a bleb of pericardial tissue in the distal lumen of the guide tube. The suction draws the bleb of pericardium into the distal port of the guide tube near the deflecting mechanism. As the penetrating end of the penetrating body is advanced distally to pierce into the pericardial bleb, the deflecting mechanism deflects the penetrating end such that the piercing tip of the penetrating body enters the bleb at an angle oblique to the longitudinal axis of the guide tube. Subsequently, a guide wire is passed through the lumen of the penetrating body and into the pericardial space. The guide tube and penetrating body are removed and a material transport tube is passed over the guidewire into the pericardial space for removal of fluid or delivery of materials therein.

At the proximal end of the pericardial access device, the handle region can include a vacuum inlet assembly for connecting an aspiration source to the device. In addition, the handle region can include a limiting mechanism for limiting the distal mobility of the penetrating body.

In some embodiments, a pericardial access device can include an exterior sheath having a reversibly sealed distal end to prevent fat, facia or other material from entering the distal end of the pericardial access device during placement. The invention also provides a method for using a pericardial access device for accessing the pericardial space.

BRIEF DESCRIPTION OF THE DRAWINGS

FIG. 2 is a longitudinal section of an embodiment of a pericardial access device of the invention.

FIG. 5 is a profile view of a penetrating body of the invention with the penetrating end deflected at an angle oblique to the longitudinal axis of the penetrating body.

FIG. 7 is a longitudinal section of the distal end of a pericardial access device enclosed in an exterior sheath with a reversibly sealed cap.

FIG. 8 is a longitudinal section of the distal end of a pericardial access device enclosed in an exterior sheath with a reversibly sealed multi-flap hatch.

FIG. 9 is a distal end view of the reversibly sealed multi-flap hatch of FIG. 9.

FIG. 10 is a longitudinal section of a third embodiment of a distal end of a pericardial access device of the invention.

DETAILED DESCRIPTION OF THE ILLUSTRATED EMBODIMENT

Figure 1:
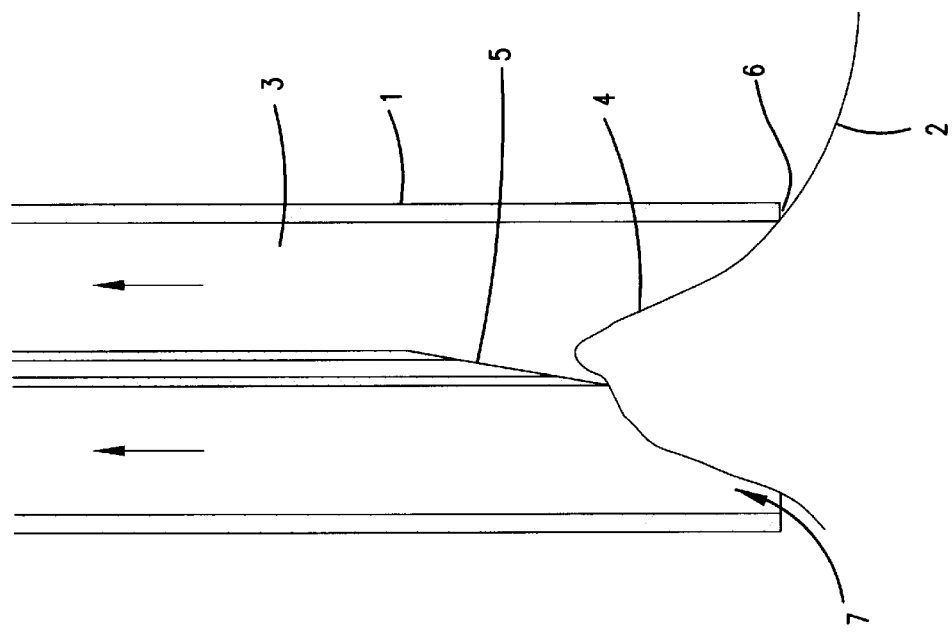
FIG. 1 is a longitudinal section of a distal end of a prior art device for accessing the pericardial space that is outside the scope of the present invention.

The invention will be described with reference to the accompanying drawings, wherein like reference numerals identify similar or corresponding components throughout the several views. The illustrated embodiments and description are for exemplary purposes to facilitate comprehension of the invention and should not be construed to limit the scope thereof. In addition, it will be noted that in several places throughout the specification, guidance is provided through lists of examples. In each instance, the recited list serves only as a representative group. It is not meant, however, that the list is exclusive.

A pericardial access device according to the present invention provides accurate local access to the pericardial space of a human or animal patient for introduction of a material therein, with a low risk of myocardial injury during access. Once the pericardial space is accessed, a material transport tube (e.g., a catheter) is inserted into the space for delivery of the desired material.

As used herein, the term "material" refers to any material that can be introduced into the pericardial space through the material transport tube including gasses, liquids or solids. Materials include pharmaceutical agents such as vasodilators, antiplatelets, anticoagulants, thrombolytics, anti-inflammatories, antibiotics, fibrinolytics, antiarrhythmics, inotropics, antimitotics, angiogenics, antiatherogenics, etc. "Material" also includes heated or cooled fluids (e.g., ice water), flowable powders, controlled drug release implants, or other solid material which can pass through a material transport tube including, for example, implantable electrical leads.

One problem with some prior systems for accessing the pericardial space using suction is illustrated in FIG. 1. As shown, when tube 1 contacts the pericardium 2 and suction (arrows) is applied to the lumen 3 of the tube 1, a bleb of pericardium 4 is formed within lumen 3. As a piercing instrument 5 such as a needle, is distally advanced to pierce the bleb 4 the bleb 4 can be pushed away from the distal end 6 of tube 1 allowing air to rush in at, for example, arrow 7, thus breaking the vacuum seal which can result in tearing or non-penetration of the pericardium.

As will be fully described herein, the present invention overcomes problems with prior art devices by penetrating the bleb with a penetrating body that penetrates the bleb at an angle that is oblique to the longitudinal axis of the guide tube. As will be appreciated, the angle of penetration of the bleb is also oblique to the plane of the distal port opening of the guide tube.

Referring to FIG. 2, there is illustrated a longitudinal cross section view of one embodiment of a pericardial access device 10 according to the invention. According to this embodiment, the device 10 has a distal end 11 including a penetrating body 12 that is axially mobile within lumen 13 of guide tube 14. The device 10 has a proximal end 15, which includes a handle region 16 for handling and operating the device during use. The handle region 16 can include a vacuum inlet assembly 17 and a guide wire port 18 for passing a guide wire 19 through the lumen 20 of penetrating body 12. According to the invention, the vacuum inlet assembly 17 need not be located in the proximal end of the device but can be located anywhere that will permit a suction force to be applied to the distal end 11 of lumen 13 of the guide tube 14.

The vacuum inlet assembly 17 includes a suction channel 21 having a distal end 22 that is in fluid communication with guide tube lumen 13. The proximal end 23 of the vacuum inlet assembly 17 includes a connector 24, such as a luer lock for connecting a suction source (not shown) to device 10. The device 10 also includes a sealing mechanism 25, such as a gasket, at a point proximal to the vacuum channel 21 which, when a suction force is applied to the guide tube lumen 13, permits axial movement of penetrating body 12 without loss of suction to the guide tube lumen 13 when the penetrating body 12 is moved.

Figure 3:
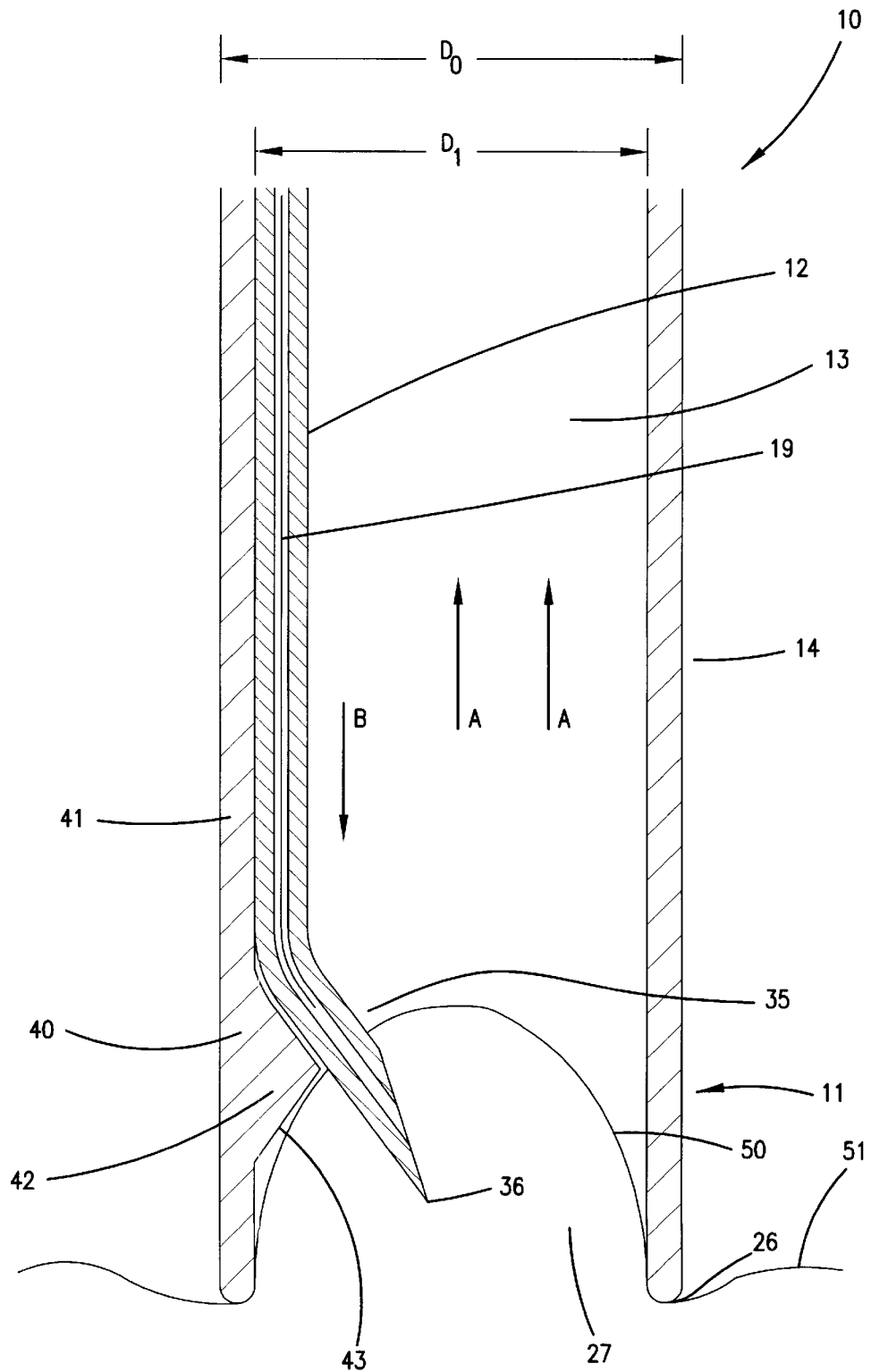
FIG. 3 is a longitudinal section of a first embodiment of a distal end of a pericardial access device of the invention.

FIG. 3 is a longitudinal section view of one embodiment of a distal end 11 of a pericardial access device 10 according to the invention. Generally, a guide tube 14 of the invention can be prepared from plastic, stainless steel, titanium, titanium alloy, ceramic or other material suitable for the herein below described function of a guide tube. At the distal end 11, guide tube 14 includes a distal tip 26 where guide tube lumen 13 opens to the exterior through a distal port 27. Thus, the distal port 27 is in a plane that is perpendicular to the longitudinal axis of the guide tube lumen 13 (Y-Y of FIG. 4). The outside diameter $D_0$ of guide tube 14 can be about 3 mm to 12 mm, typically about 6 mm to 8 mm. The diameter $D_1$ of the guide tube lumen 13 can be about 2 mm to 11 mm.

Figure 6:
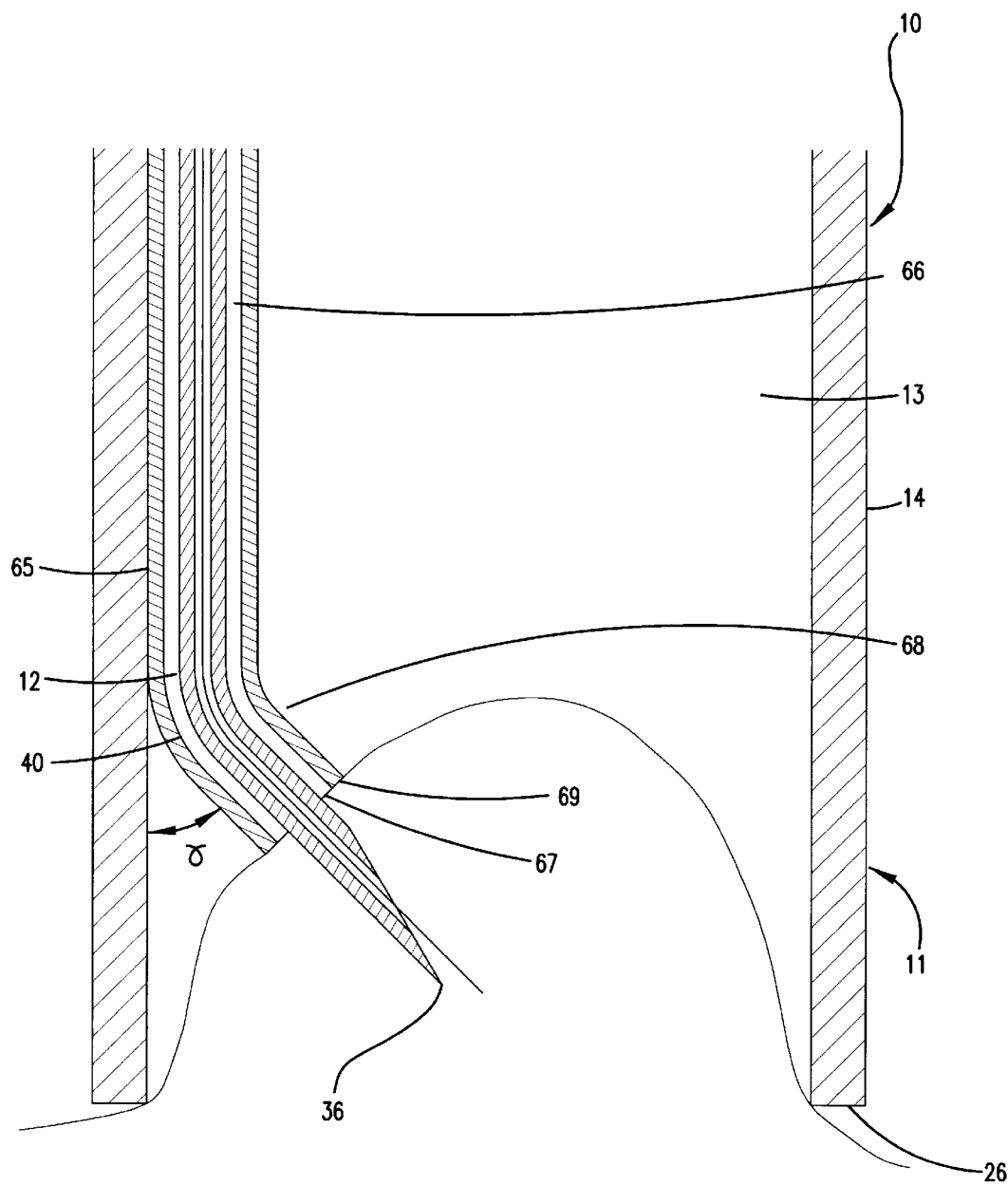
FIG. 6 is a longitudinal section of a second embodiment of a distal end of a pericardial access device of the invention.

FIG. 5 is a profile view of a penetrating body 12, removed from guide tube 14 (not shown in FIG. 5). The penetrating body 12 is an elongate body having a distal penetrating end 35 with a sharp piercing tip 36 for penetrating the pericardium. The diameter of the penetrating body 12 should provide for axial mobility within the guide tube lumen 13. The inside diameter of the guide tube lumen should allow for passage of guide wire 19. In a typical embodiment the guide wire diameter can be about 0.2 mm to 0.8 mm. In FIG. 6, the penetrating end 35 of the penetrating body 12 is deflected to have an oblique angle ($\gamma$) for penetrating a pericardial bleb. A proximal end 37 of the penetrating body 12 extends to the handle region 16 (FIG. 2). A proximal end opening 39, or guide wire port 18, (FIG. 2), provides access to lumen 20 which passes through penetrating body 12. The lumen 20 opens distally at piercing tip 36 such that lumen 20 provides a channel for passing guide wire 19 (FIG. 2) from guide wire port 18 through the penetrating body and out the piercing end into the pericardial space.

Figure 4:
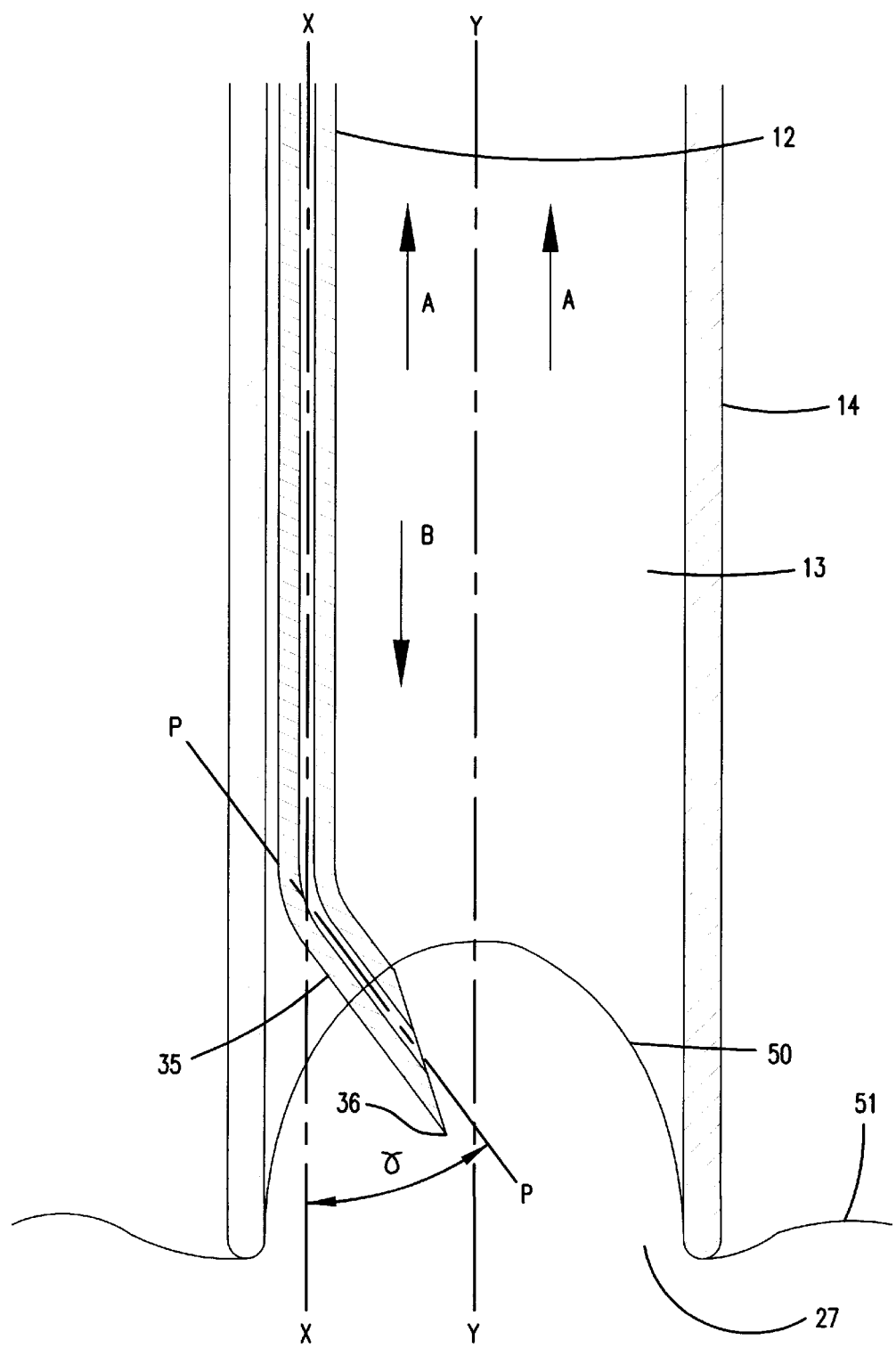
FIG. 4 is a longitudinal section of the distal end of a pericardial access device of the invention (omitting a deflecting mechanism for clarity) illustrating various axes of components of the device and an oblique angle of the penetrating body relative to a pericardial bleb.

FIG. 4 illustrates the various axes of the penetrating body relative to the guide tube axis Y-Y. Referring to FIGS. 4 and 5, the penetrating body 12 has a longitudinal axis X-X parallel to the longitudinal axis Y-Y of guide tube 14. In addition, in use, the penetrating body 12 also has a second axis or "penetrating axis" P-P. The penetrating axis P-P is at an angle $\gamma$ relative to longitudinal axes X-X and Y-Y and is an axis through which the piercing tip 36 of penetrating body 3 penetrates a bleb 50 (described below) formed in the guide tube lumen 13. According to the invention, angle $\gamma$ is generally about 20° to 80°, typically about 30° to 60°, in some embodiments, $\gamma$ is about 45°.

Referring to FIGS. 3 and 4, in use a suction force (arrow A) is applied to lumen 13 of guide tube 14 to form bleb 50. As used herein, a "bleb" refers to the parietal pericardial tissue 51 which is drawn into the lumen 13 of guide tube 14 through distal port 27 when suction is applied to lumen 13. Once bleb 50 is formed, the penetrating body 12 is distally advanced (arrow B) towards bleb 50. A deflecting mechanism 40 deflects the penetrating end 35 of penetrating body 12 to angle $\gamma$ causing the piercing tip 36 to penetrate the bleb 50 along axis P-P. Thus, as illustrated in FIG. 4, during use, the direction of the suction flow (arrows A) is substantially parallel to the longitudinal axis X-X of penetrating body 12 and the longitudinal axis Y-Y of guide tube 13. Hence, penetrating axis P-P of the penetrating body 12 has the same angular relationship $\gamma$ to the longitudinal axis of the penetrating body X-X, guide tube Y-Y and the direction of suction flow (arrows A). Angle $\gamma$ is about 20° to 80°, typically about 30° to 60°, and, in some embodiments, about 45°.

The penetrating body 12 can be prepared from any material that can resist deformation when functioning to pierce the pericardium. In addition, the material of the penetrating body, at least at the penetrating end, should be able to be deflected by the deflecting mechanism to angle $\gamma$. Suitable materials for a penetrating body include, for example, stainless steel, titanium, titanium alloys (e.g., Ni—Ti), etc.

FIG. 3 illustrates one embodiment of a deflecting mechanism 40 for deflecting the penetrating end 35 of a penetrating body 12. According to this embodiment, the distal end of a wall 41 of guide tube 13 is constructed to include a deflecting wedge 42 to deflect penetrating end 35 to angle $\gamma$. The base 43 of the deflecting wedge preferably does not extend completely to distal opening 27 to allow for formation of a suitable bleb 50. In use, a linear penetrating body 12 is advanced distally in the guide tube lumen 13. As the penetrating end 35 moves distally past deflecting mechanism 40, the penetrating end 35 is deflected to form axis P-P through which piercing tip 36 penetrates bleb 50. Axis P-P is at an angle $\gamma$ oblique to the longitudinal axis Y-Y of guide tube 14. It will be appreciated that axis P-P also forms an angle $\gamma$ relative to axis X-X of penetrating body 12 that is proximal to the deflecting mechanism 40.

FIG. 6 illustrates the distal end 11 of another embodiment of an access device 10 of the invention. According to this embodiment, the deflecting mechanism 40 includes a deflecting tube 65 mounted within lumen 13 of guide tube 14. The deflecting tube 65 has a distal tip 69 and a lumen 66 through which penetrating body 12 can pass from the proximal end (not shown) to the distal opening 67 at distal tip 69. The proximal end of the deflecting tube need not extend to the proximal end 15 of the device. The deflecting tube 65 includes a deflecting tube end 68 that is configured at an oblique angle $\gamma$ relative to axis Y-Y of guide tube 14. The angle $\gamma$ of deflecting end 68, relative to guide tube axis Y-Y is about 20°–80° typically about 30°–60°, and, in some embodiments, about 45°. In the embodiment of FIG. 6, as the penetrating body is advanced distally, the deflecting end 68 deflects the penetrating end 35 of penetrating body 12 to form piercing axis P-P, the axis through which piercing tip 36 penetrates bleb 50. The distal tip 69 of deflecting tube 65 does not extend to the distal tip 26 of guide tube 14. Rather, the distal tip 69 stops proximal to the guide tube distal tip 26 to allow for formation of a suitable pericardial bleb 50 in the distal end 11 of lumen 13.

In addition to a deflecting mechanism as described herein, it will be appreciated that other deflecting mechanisms which function to deflect the distal end of a penetrating body as disclosed herein are within the skill of one in the art and fall within the scope of the present invention.

FIG. 10 illustrates a further embodiment of a device of the invention. According to this embodiment, the distal end 11 of guide tube 14 includes a deflecting mechanism 40, and further includes an axial projection 70 or shoulder 71 at distal tip 26, near distal port 27. According to this embodiment, the diameter $D_2$ of guide tube lumen 13 is narrowed by the axial projection 70. The axial projection has a longitudinal dimension $D_3$ and an axial dimension $D_4$. The longitudinal dimension $D_3$ and axial dimension $D_4$ of shoulder 71 determines the aspect ratio at the distal end of lumen 13. As used herein, "aspect ratio" is the ratio of the hole diameter to cylinder length (i.e., $D_2:D_3$). According to the invention, the hole diameter $D_2$ should be greater than the cylinder length, i.e., $D_2>D_3$. The aspect ratio is generally, at least 1:1, typically greater than about 2:1, preferably greater than 4:1. Once the bleb 50 is formed in the distal end 11 of lumen 13, the shoulder 71 buttresses the bleb 50 in a position that reduces the likelihood of the pericardium (not shown in FIG. 10) from moving away from the distal tip 26 of guide tube 14 when bleb 50 is contacted by the distally advancing piercing tip 36 of penetrating body 12.

The shoulder 71 can be continuous around the circumference of lumen 13 or intermittent. As used herein, "intermittent" refers to a shoulder that has gaps around the circumference of the lumen but still functions to buttress the bleb as described above. It will be appreciated that other shoulder constructions that are not illustrated here but which provide the described function are within the scope of the present invention. Alternative embodiments of shoulder configurations are disclosed in copending U.S. Ser. No. 08/933,858 the entire disclosure of which is incorporated by reference herein.

In some embodiments, the axial travel of penetrating body 12 within guide tube lumen 13 is limited to prevent piercing tip 36 from traveling distally beyond distal port 27 of guide tube 14 which could result in penetration of the myocardium. Preferably, however, the distal travel of penetrating 12 body is stopped before extending beyond distal tip 26 of guide tube 14. Referring to FIG. 2, in one embodiment, a limiting mechanism 55 is located in the handle region 16 of the device 10. As shown in FIG. 2, the limiting mechanism 55 can include a collar 56 attached to the proximal end of penetrating body 12. Distal travel of penetrating body 12 is stopped when collar 56 contacts the proximal aspect 57 of vacuum inlet assembly 17. In the illustrated embodiment, collar 56 is fixed to sleeve 52 which provides a grip for rotating or moving the penetrating body 12 axially. In alternative embodiments a limiting mechanism can be located in the distal aspect of the guide tube to provide for limiting the axial travel of the penetrating body.

During use of a pericardial access device according to the invention, an incision of sufficient size for passage of guide tube is made in the thoracic wall, for example in the subxiphoid region, using known methods. A second incision can be made for insertion of an endoscope into the thoracic cavity for visualization of the access procedure. Alternatively, the access procedure can be visualized with the aid of known external visualization systems such as fluoroscopy, ultrasound, etc. In a subxiphoid approach, for example, the device is advanced percutaneously through the first incision over the diaphragm into the mediastinal space until the distal end of the device contacts the pericardial surface of the heart. The device is aligned at a desired location on the pericardial surface of the heart and suction is applied to the guide tube lumen to form a bleb of pericardial tissue through the distal port within the guide tube lumen. Once the bleb is formed, the piercing tip of the penetrating body is advanced distally to pierce the bleb. A guidewire is then passed through the guidewire port, through the lumen of the penetrating body and into the pericardial space. The device is removed and a catheter or other known material transport tube is passed over the guidewire into the pericardial space. The guidewire can be removed during fluid removal or administration of the desired material into the pericardial space. With a distal end of the material transport tube located in the pericardial space, a proximal end of the material transport tube can be fixed outside the patient's body, using known methods, for long or short term access to the pericardial space through the material transport tube.

A pericardial access device according to the invention can be freely advanced through the skin incision to the pericardial surface of the heart for accessing the pericardial space. Alternatively, an introducer or cannula can be passed through the skin incision to the pericardial surface and the pericardial access device passed through the introducer to the pericardial surface. Referring to FIGS. 7–9, in another alternative, the pericardial access device 10 can be passed to the pericardial surface within an exterior sheath 60 having a reversibly sealed distal end 61. In the embodiment of FIG. 7, the distal end 61 of the exterior sheath 60 is reversibly sealed with a removable cap 62. The cap 62 is securely attached to the sheath 60 by a base 63. The removable cap 62 can be forced open by distal advancement of the device 10 within sheath 60.

Alternatively, as shown in FIGS. 8 and 9, the distal end 61 of sheath 60 can be reversibly sealed by a multi-flap hatch 64. Distal advancement of the access device 10 opens the multi-flap hatch 64 distally to allow exteriorization of the distal tip 26 of the device 10. Therefore, according to this embodiment, the exterior sheath 60, including the pericardial access device 10, is passed through the skin incision to a position near, but not contacting, the pericardial surface. Once at the desired position, guide tube 14 of the device 10 is distally advanced to open the cap 62, or the multi-flap hatch 64, allowing the distal tip 26 of the guide tube 14 to contact the pericardial surface at the desired location for placement of the material tube. Thus, the exterior sheath can function to prevent fat, facia or other material from traveling retrograde into the lumen of the guide tube during placement.

It will be apparent to one of ordinary skill in the art that many changes and modifications can be made in the invention without departing from the spirit or scope of the appended claims.

I claim:

1. A pericardial access device comprising:
   (a) a non-piercing guide tube, said non-piercing guide tube having a lumen and including:
      (i) a proximal end;
      (ii) a distal end, said distal end having a distal port opening into said lumen;

(iii) a longitudinal axis;
(iv) a deflecting mechanism; and
(b) a penetrating body axially mobile within said guide tube lumen, said penetrating body including:
(i) a proximal end; and
(ii) a penetrating end having a penetrating axis
wherein, when said penetrating body is advanced distally within said guide tube lumen past said deflecting mechanism, said deflecting mechanism deflects said penetrating end such that said penetrating end axis is at an angle oblique to said non-piercing guide tube longitudinal axis.

2. A pericardial access device according to claim 1 wherein said oblique angle is about 20°–80°.

3. A pericardial access device according to claim 1 wherein said oblique angle is about 30°–60°.

4. A pericardial access device according to claim 1 wherein said deflecting mechanism is a wedge within said non-piercing guide tube lumen near said distal port opening.

5. A pericardial access device according to claim 1 wherein said deflecting mechanism is a deflecting tube.

6. A pericardial access device according to claim 1 wherein said proximal end of said non-piercing guide tube includes to a handle region.

7. A pericardial access device according to claim 6 wherein said handle region includes a limiting mechanism for limiting axial mobility of said penetrating body.

8. A pericardial access device according to claim 1 wherein said proximal end of said non-piercing guide tube includes a vacuum inlet assembly.

9. A pericardial access device according to claim 1 further comprising a guide wire.

10. A pericardial access device according to claim 9 further comprising a material transport tube.

11. A pericardial access device according to claim 1 wherein said distal end of said non-piercing guide tube further includes an axially directed shoulder in said lumen near said distal port.

12. A pericardial access device according to claim 1 further including an exterior sheath.

13. A pericardial access device according to claim 12 wherein said exterior sheath includes a reversibly sealed distal end.

14. A method for accessing the pericardial space of a patient comprising:
(a) passing a tubular device to a patient's pericardium, said tubular device including:
(i) a guide tube, said guide tube including:
a longitudinal axis;
a lumen having a distal port at a distal end of said guide tube; and;
(ii) a penetrating body having a penetrating end and a piercing tip for penetrating a pericardial bleb;
(b) contacting said patient's pericardium with said distal end of said non-piercing guide tube;
(c) applying a suction force through said lumen of said guide tube to form said bleb from said patient's pericardium within said lumen of said guide tube; and
(d) advancing said penetrating body distally in said guide tube lumen such that said penetrating end is at an angle oblique to said longitudinal axis of said guide tube when said piercing tip penetrates said bleb of pericardium.

15. A method according to claim 14 wherein said oblique angle is about 30° to 60°.

16. A method according to claim 14 wherein said guide tube includes a deflecting mechanism.

17. A method according to claim 16 wherein said deflecting mechanism is a wedge.

18. A method according to claim 16 wherein said deflecting mechanism is a deflecting tube.

* * * * *